(12) United States Patent
Perlman

(10) Patent No.: US 10,696,936 B1
(45) Date of Patent: Jun. 30, 2020

(54) SYSTEM FOR ENVIRONMENTAL MICROBIAL TESTING

(71) Applicant: Perlman Consulting, LLC, Arlington, MA (US)

(72) Inventor: Daniel Perlman, Arlington, MA (US)

(73) Assignee: Perlman Consulting, LLC, Arlington, MA (US)

( * ) Notice: Subject to any disclaimer, the term of this patent is extended or adjusted under 35 U.S.C. 154(b) by 0 days.

(21) Appl. No.: 16/237,085

(22) Filed: Dec. 31, 2018

(51) Int. Cl.
*C12M 1/00* (2006.01)
*C08B 37/00* (2006.01)
*C12N 5/00* (2006.01)

(52) U.S. Cl.
CPC ......... *C12M 23/20* (2013.01); *C08B 37/0045* (2013.01); *C12N 5/0018* (2013.01)

(58) Field of Classification Search
CPC .................................................... C12M 23/20
See application file for complete search history.

(56) References Cited

U.S. PATENT DOCUMENTS

| 4,241,186 A | 12/1980 | Roth | |
| 4,268,533 A * | 5/1981 | Williams | ................. A23L 9/10 |
| | | | 426/271 |
| 4,282,137 A | 8/1981 | Roth | |
| 5,698,260 A | 12/1997 | Roth | |
| 2011/0027866 A1 | 2/2011 | Roth | |

OTHER PUBLICATIONS

Jayaram et al., Klimik Derg, 2018, 31(1):11-15.*
Jayaram, M. et al., "Potato Dextrose Agar with Rose-Bengal and Chloramphenicol: A New Culture Medium to Isolate Pathogenic Exophiala dematitidis From the Environment", Klimik Dergisi, 2018, 31(1): 11-15 DOI: 10.5152/kd.2018.05.

* cited by examiner

*Primary Examiner* — Bin Shen
(74) *Attorney, Agent, or Firm* — Verrill Dana, LLP

(57) ABSTRACT

A gelled biological growth medium in a culture container, as well as kits and methods of producing the growth medium, utilize gelling of a liquid growth medium containing low methoxyl pectin on a film of calcium salt deposited on a growth surface of the culture container. The salt acts as a trigger for gelation and is conveniently deposited on the walls by evaporation of methanol or another volatile solvent.

17 Claims, 2 Drawing Sheets

SYSTEM FOR ENVIRONMENTAL MICROBIAL TESTING

BACKGROUND

Methods for controlled cultivation of microorganisms on the surface of gelled media are in widespread use. Techniques have been developed to study bacteria, fungi, mosses, and eukaryotic cells and tissues. Gelled media are also used in environmental microbial testing.

Awareness of environmental hazards has led to an increased desire to conduct microbial testing, and microbial test kits are available for such testing. For practical microbial field testing, it has become necessary to conduct such testing without the use of heating and/or laboratory sterilization of culture media in the field, and without the use of equipment such as autoclaves, glove boxes, or biological hoods in the field.

Agar is a commonly utilized gelling material for microbial culturing in Petri dishes and the like. Agar is derived from algae and includes a mixture of the polysaccharide agarose together with agaropectin. Agar has been used for many decades to solidify nutrient-containing growth media used for culturing and identifying different species of bacteria, yeasts and molds. A suspension of agar powder in liquid nutrient medium is typically boiled to dissolve the constituent polysaccharides, sterilized, and then cooled to approximately 50-60° C. before pouring the liquid medium into a culture container such as a glass or polystyrene Petri dish. The preparation of a sterile agar Petri dish typically requires specialized skill in sterile techniques and in preparation of the agar or other suitable growth media.

The availability of simplified and more rapid preparation methods for gelled culture media would improve the convenience and utility of microbial testing in the field such as in residential homes, manufacturing facilities and businesses, especially when performed by persons without specialized skills or equipment.

SUMMARY

The present technology relates to the field of sterile biological culture media and provides methods and kits for making an easily and rapidly gelled sterile culture medium, that includes pectin as the gelling agent. Final preparation and sterile provision of a microbial sampling and culturing container with culture medium can be performed without access to special equipment or techniques, and can be performed without specialized training or equipment.

A pectin-based gelling system providing a source of calcium ions to gel and solidify a nutrient medium obviates the need to boil or otherwise heat or reheat a cell culturing medium immediately before pouring the medium into a Petri dish. Therefore, it is well suited for field work and consumer use where controlled heating/sterilization may be impossible or inconvenient. The present technology provides a system for production of such growth media, the system for microbial analysis and oversight by those with skill in the art, where the growth media can be distributed to end users who possess ordinary skill, the growth media provided in a kit with instructions. The present technology moves the preparation of biological growth media to the hands of more users by providing sterile methods for producing gelled culture media that can be followed quickly and, for example, in remote locations.

The present technology provides a kit. The kit overcomes difficulties in preparing biological growth media, for example, sterilization of the container, sterilization of the medium, transportation and assembly of the biological growth system, time involved, and necessary end-user skill. Final preparation of the biological growth medium from the kit involves no specialized skill in microbiology or in the preparation of sterile growth media. Instead, persons preparing the biological growth media follow general methods and instructions described therein. The present technology also involves methods of preparation of biological growth media and methods of using the prepared media including specialized containers designed for use.

The present technology utilizes pectin for gelling of growth media, and no agar is needed. An aspect of the system is the preparation and sterilization of a growth media containing amidated low methoxy pectin along with nutrients. While unmodified low methoxy (LM) pectin can be used in the present technology, the use of a chemically modified LM low ester pectin that has been altered by amidating the pectin is beneficial. Such an amidated pectin is sometimes referred to as an LA pectin or even an LMA pectin. The amidated pectin molecules are modified by converting some of the galacturonic acid residues to carboxylic acid amides (e.g., using ammonia) and the resulting pectins can form strong gels over a wider range of calcium concentrations than unmodified LM pectins.

In one example, these LA pectin soluble solids are contributed in dissolved potato dextrose broth or "PDB" (obtained from Alpha Biosciences, Baltimore, Md.) that includes 2% dextrose and 0.4% potato extract, where as little as 2% by weight of added LA pectin is sufficient to solidify the broth using approximately 15-60 mg calcium per gram of pectin without substantial syneresis (release of free liquid from the gel) occurring. Two examples of amidated low ester pectins that have been successfully used at a level of 2% by weight pectin to form gelled PDB nutrient growth medium herein include LA 410 pectin obtained from DuPont Danisco USA (New Century, Kans.) and amidated low methoxy pectin LM 35 obtained from TIC Gums, Inc. (White Marsh, Md.). While these examples do not limit the present technology, many more suppliers of amidated low ester pectins are available.

In another example, chloramphenicol (IBI Scientific, Dubuque, Iowa) is also included as a broad spectrum antibiotic agent at a level of approximately 50-100 micrograms/milliliter in the pectin-containing PDB nutrient growth medium for inhibiting bacterial growth and selectively detecting the presence of airborne mold spores.

In another example, the pectin-containing growth medium can be produced with specific nutrients to promote growth of targeted cells or, as in the example above, specific agents to prevent growth of undesired biologics. The kits produced by the system described herein can be targeted to selectively cultivate microbes or other cells or tissues, e.g., bacteria or molds or cells or tissues of higher eukaryotes, and the growth medium contained therein can be tailored for the needs of the end user.

Typically, LM pectins may be gelled using between approximately 15 mg and 30 mg of calcium per gram of pectin. However, between 10 and 60 mg, or even as high as 90 mg, calcium per gram of pectin can be used in the LA gels, containing surprisingly low levels of dissolved solids, without excessive syneresis occurring even 1-2 days after forming the gel. Syneresis would normally be expected to occur as calcium ions cause contraction of the gel as pectin polysaccharide molecules are drawn closer together by calcium ions. Syneresis in a Petri dish is problematic in some examples. When attempting to detect and count the number of environmental mold spores or bacteria settling on a solid culturing medium, free water on a solid culturing medium can allow multiplying mold cells and also bacteria cells to spread away from their initial contact point and then confuse the measurement. Syneresis would be expected to be particularly problematic when only low levels of dissolved solids, a.k.a., soluble solids, are present in the gel. For example, in some nutrient gels produced herein for culturing and detecting mold spores the gels contain as little as 2.4% by weight of soluble solids.

Using the production methods disclosed herein, the growth medium with pectin is placed in a secure package after preparation. Sterilization of the growth medium can be done before, during, or after packaging, using sterilization techniques known in the art. The package is suitable for storage and transportation, and the sterilized growth medium does not gel until it comes into contact with a gelling agent, which contains calcium. While the package of growth medium is suitable for storage and transportation, the package is preferably supplied within a kit, and the kit can be packaged to further ensure stability during storage/transportation. Alternatively, the entire kit can be sterilized after assembly but before shipping, for example, by irradiation, pasteurization, or microwaves.

Using the methods of production disclosed herein, a solution of calcium lactate is prepared in methanol, and the methanol sufficiently sterilizes the solution. Enough methanol is used to dissolve the calcium lactate. The calcium provided by this solution is utilized as a gelling agent for the pectin-containing growth media. This gelling agent solution is securely packaged and is suitable for storage and transportation. Alternatively, other alcohols such as ethanol or isopropanol may be added to the methanol solution of calcium lactate but in proportions to preferably not cause precipitation of the calcium lactate. The package of gelling agent is preferably supplied within a kit that includes a cell culture container, along with the package of growth media described above, and the kit can be packaged to further ensure stability during storage/transportation. If other soluble organic salts of calcium are utilized to form a film in the cell culture container, the salts may dissolve and be either moderately or highly soluble in methanol, or alternatively the organic salts may form a slurry with the organic salts being either poorly, moderately or highly soluble in methanol or other volatile solvent, and the slurry still performs the intended function(s).

In an embodiment, the kit contains a package of pre-sterilized pectin medium, a package of pre-sterilized calcium lactate in methanol solution, a Petri dish or another container with lid all pre-sterilized, and instructions for use. In some cases, instructions/methods are included with the kit or printed on the container(s). In other cases, instructions are transmitted by email, website, text message, or other electronic means. The end user of the kit follows the instructions and can quickly cause the gelling of a sterile pectin-containing growth medium using the kit and method provided.

Another aspect of the present technology is a method of use wherein the person conducting the microbial sampling, e.g., exposure to air or water by the end user, follows instructions so that a container of pre-sterilized calcium lactate solution in methanol is opened and poured into a pre-sterilized Petri dish or similar container. The end user ensures that at least the bottom interior surface of the Petri dish or container is evenly covered by the solution. The end user then waits for the methanol to evaporate, at least depositing a consistent film of calcium lactate upon the bottom of the container. Then the pre-sterilized pectin-containing growth medium is poured into the Petri dish or similar container, and the lid to the container is applied. After a brief time interval, the pectin forms a gelled growth medium that is ready for use, e.g., ready for exposure to air, water samples and/or other materials containing possible microbial contaminants. Formation of the gel can be established by picking up the container in the hand and noting that the gel does not tilt within the container. This method of the present technology enables an end user to prepare a sterile solidified growth medium far from sterilization equipment such as autoclaves, glove boxes, or biological cabinets.

In an embodiment, the system of the present technology produces a kit containing a package of pre-sterilized pectin medium, a package containing a Petri dish or similar container, with the Petri dish already containing a dry uniform internal coating of calcium lactate, at least upon a portion of the container, all pre-sterilized, and instructions for use. In this embodiment, the end user of the kit opens the Petri dish, pours the pectin-containing growth medium into the dish, places the lid upon the dish, and waits a brief time, e.g., 15-30 minutes for a gel to form. The uniformity of a dried coating (preferably in the form of a precipitate or film deposited on a growth surface of the dish) of calcium lactate in a Petri dish or other culture container, that assures the uniformity of pectin gel formation over the cell growth surface of the dish, can be visually monitored before adding the growth medium. This monitoring can be facilitated by a white translucent or semi-opaque appearance of the dried adherent calcium lactate coating on the dish. If any area on the dish has been poorly or deficiently coated, that area appears more transparent/less opaque. Where methanol has been used to solubilize the calcium lactate, the white appearance of a calcium lactate coating can be adjusted by including a small amount of water, e.g., approximately 2%-4% by volume, in the methanol as the calcium lactate crystallizes on the surface of a cell culture container. It is believed that this level of moisture provides crystalline water of hydration that enables some or most of the calcium lactate to precipitate in the form of calcium lactate pentahydrate crystals that scatter light and thus appear white. By comparison, an anhydrous calcium lactate coating that is precipitated from anhydrous methanol produces a nearly invisible clear transparent coating on the surface of a Petri dish or other cell culture container.

In embodiments, the manufactured kit can be sold at retail to those with ordinary skill who seek to perform microbial testing or who, for example, seek to cultivate bacteria, moss, or fungi on a medium. In another example, the kits are produced by a quality assurance group and distributed to hospitals in various locations for use by quality sampling groups. The kits produced herein are durable for transportation and storage. Potentially the kits described herein could be shipped to far reaches for specific explorations.

In an embodiment, the disclosed system involves calculation of an amount of pre-sterilized pectin media, sufficient for a certain size container. The system also involves preparation of pre-sterilized calcium lactate solution in methanol, in amount sufficient to gel the pectin media and to coat, at least the bottom interior surface of, a certain size container, and placement of this solution into a sealed container for later use. The system also involves secured placement of a pre-sterilized or cleaned Petri dish or similar container, with known internal area, with lid onto container, for example a sealed box of suitable material, along with the container of pectin media and container of calcium lactate solution, sealing the box, and transporting or shipping the box to the person conducting the microbial testing.

In an alternative embodiment, only the package of pre-sterilized pectin growth media and the package of pre-sterilized calcium lactate solution is shipped to the end user conducting the microbial testing, and this person already has suitable sterile containers with lids. Instructions for use could be provided with the packages, printed on labels, or sent by e-mail or other electronic means.

The persons using the kit disclosed herein can conduct microbial testing or biological cultivation and can follow general instructions for preparation of the microbial testing kit and subsequent brief or controlled exposure of the gelled medium to the environment such as exposure intervals of approximately 10 min to 4 hr, or approximately 30 min to 2 hr, or approximately 1 hr. For example, the kit may travel with a health inspector, who uses the kit on-site to sample food from a vendor or water from a drinking well. Potentially an archeologist obtains the kit to sample microbes from a sealed location that has not been unsealed for thousands of years. The present technology uniquely provides a kit that can be opened and can provide sterile microbial testing media in a remote environment in a short time, surprisingly, even after the kit has been in transportation and/or storage for a considerably long time.

If desired, the shelf-life of the kit discussed herein can be extended, for example, by secured sterile packaging, use of ultra-high-temperature processing during manufacture, irradiation, additives, or other means known in the art. The system disclosed herein also includes determination of kit shelf-life, if desired, by stability testing under various accelerated conditions and/or subsequent prediction of shelf-life using techniques known in the art.

The liquid growth medium may contain liquid growth medium with other added ingredients, for example, preservatives, blood cells, pH indicators, neomycin, beef broth, gentamicin, indicators, nutrients, soy, and buffers.

One experienced in the art will recognize the significance of the present technology in expanding the provision of growth media to end users, and it is understood that embodiments of the present technology encompass various systems, methods, and physical constructions, within the idea of the technology. The system, method(s) and embodiment(s) are further described below.

The covered or uncovered growth container, in an embodiment, contains an internal surface coating or film of calcium lactate deposited from evaporation of methanol, the surface coating or film at least sufficiently coating the bottom interior surface of the container, the container suitable for gelling of a liquid growth medium containing low methoxyl pectin or amidated low methoxyl pectin material, with, for example, the coating or film of calcium lactate able to be converted from anhydrate forms to hydrate crystalline forms or and/or proportions of various hydrated forms without affecting the suitability for gelling of the liquid growth medium.

The present technology, in an embodiment, is a calcium lactate film (consisting essentially of a solid form of calcium lactate salt deposited as a layer) adhered to a transparent plastic or glass surface, wherein said film is cast on said surface by evaporation from a solution comprising calcium lactate and at least some methanol. This film is remarkable in being durable and tightly bound to the surface (either glass or polystyrene or polylactide thermoplastic, for example) in which the film can be transparent or translucent yet white or whitish in color. The film may or may not contain crystals of calcium lactate visible with a microscope or the unaided eye. If some water is present in the methanolic calcium lactate solution, the resulting film is whitish translucent. If the calcium lactate solution is anhydrous methanol, the resulting film is transparent. The film is useful in slowly dissolving and releasing free calcium ions (i.e., divalent cations of calcium) into a nutrient cell culture medium comprising a dissolved calcium-reactive pectin that can be gelled by the calcium ions. In this regard, the film containing a calcium salt, such as calcium lactate, is preferably not present in or embedded in another material, such as a gel, polymer matrix, a plurality of microparticles or nanoparticles, or a water insoluble material or coating, but is present as a salt material substantially free, essentially free, or entirely free of other materials, particularly water-insoluble materials, so as to promote optimal dissociation of the salt and release of calcium ions when a gellable growth medium is added to the culture container and contacts the calcium salt film. This embodiment of the technology can be provided to the end-user along with sterile pectin-containing growth media and instructions, all in a kit.

The method of preparation, in an embodiment, is performed wherein said liquid growth container is a Petri dish and the amount of a volatile solvent liquid is between 0.5 mL and 2 mL per 90 mm diameter (approximately 64 cm$^2$ bottom interior surface area) Petri dish, equivalent to between 0.0078 mL and 0.0313 mL per square centimeter of Petri dish area, or between 0.005 mL and 0.050 mL per square centimeter of Petri dish area, or between 0.001 mL and 0.100 mL per square centimeter of Petri dish area, or wherein the entire interior surface area of the Petri dish is calculated in place of the surface area of the bottom interior surface of the Petri dish and substituted for the abovementioned value ranges.

Ensuring that about 2% to 5% water is contained in the methanol solution of calcium lactate has been found to be beneficial because the presence of this small amount of water results in the calcium lactate coatings drying with a whitish translucent appearance. The whitish translucent appearance is beneficial in confirming that the calcium lactate coating is uniform across the entire surface of the Petri dish or other container. Dried coatings of calcium lactate from anhydrous methanolic solutions are transparent and more difficult to monitor for coating uniformity.

The volume percentage of methanol can vary, for example, within the range of volume percentages selected from the group consisting of between 1% and 100% methanol, between 7% and 100% methanol, between 50% and 100% methanol, between 90% and 100% methanol, and between 99% and 100% methanol.

The amount of calcium lactate is variable, for example, and is within the range of between approximately 25 mg and 100 mg anhydrous calcium lactate per 0.3 g of low methoxyl pectin in approximately 15 mL of said liquid growth medium, equivalent to between approximately 85 mg and 350 mg anhydrous calcium lactate per gram of said pectin.

The amount of calcium lactate is within the range of between approximately 25 mg and 100 mg, or as high as 200 mg, of anhydrous calcium lactate per 0.3 g of low methoxyl pectin in approximately 15 mL of said liquid growth medium, equivalent to between approximately 85 mg and 350 mg, or may be as high as 700 mg, of anhydrous calcium lactate per gram of said pectin.

The kit, method, or system described herein, can also be embodied wherein the end user sends the biologic, which has grown upon the culture media, back to the originator of the kit for analysis.

The kit may enable preparation of the pectin-gelled sterile growth medium from the kit in which preparation may be in any of a variety of harsh environments. Accordingly an alternative embodiment is the kit, method, or system described herein, wherein a pre-formed calcium lactate film is provided, for example, within a flexible growth container, and the packaged growth medium is released within the growth container by applying pressure to the flexible growth container. In this example the packaging is ruptured by external pressure on the growth container by the end user. In another embodiment, the package or packages are opened external to the container by pressure or by breaking only a portion of the package. The growth medium and the calcium lactate solution may both be contained in rupture packages. The presently disclosed technology encompasses various forms of packaging and is not limited to the presently disclosed packages.

The user may wait 5 to 60 minutes, 10 to 40 minutes, 10 to 20 minutes, 15 to 30 minutes, 20 to 45 minutes, 20 to 25 minutes, 15 to 20 minutes, 30 to 120 minutes, or 40 to 180 minutes for the growth medium to gel. In a normal ambient environment, pectin-containing cell culture media described herein can gel to a non-fluid useful state for physical handling when added to a calcium lactate-coated Petri dish in as little as 10-20 or 10-30 minutes. Alternatively, the user may wait for a period of time that is not pre-determined due to, for example, unforeseen environmental conditions or temperatures in a harsh environment.

In a method described herein, the calcium lactate can be replaced by another salt, for example, a fine powder of calcium fumarate anhydrous, calcium malate anhydrous, or calcium gluconate. Preferably, the substitute salt forms a slurry/suspension with a volatile organic solvent, such as methanol. If a slurry is used, the Petri dish or container containing the slurry can be tilted back and forth by the end user to uniformly coat the bottom of the Petri dish or container before allowing the slurry to dry. If a slurry is used, the culture medium may take longer to gel and can take, for example, from 1 to 2 hours. Therefore, calcium lactate may be partially/wholly replaced by another organic salt of calcium or a combination of calcium salts, so long as the purpose of providing a container of sterile gelled growth medium is achieved.

The methods and kits described in any of the above embodiments can comprise any organic calcium salt that is sufficiently soluble, i.e., highly or moderately soluble in a volatile solvent, for example, methanol or other volatile solvent, with or without calcium lactate, or may form a slurry in a volatile solvent.

The kit, method, or system described herein may include or embody any of the following methods or processes wherein the end-user applies the calcium lactate solution to the container on a flat surface and waits for methanol evaporation, wherein the end user applies the calcium lactate solution to the container and gently moves the container to ensure an even coating of calcium lactate solution, wherein the end user applies the calcium lactate solution to the container and applies heat or air to aid solvent evaporation or other purposes, or wherein the end user applies the calcium lactate solution by use of the packaging provided. In alternative embodiments, a different organic salt of calcium is utilized, and the end user applies a slurry of the organic salt to the container and evenly distributes the slurry.

Calcium lactate salt can be used in anhydrous form or as a hydrate. Additionally, the presently disclosed technology encompasses all possible isomers of calcium lactate or other organic calcium salts.

DETAILED DESCRIPTION

Figure 1:
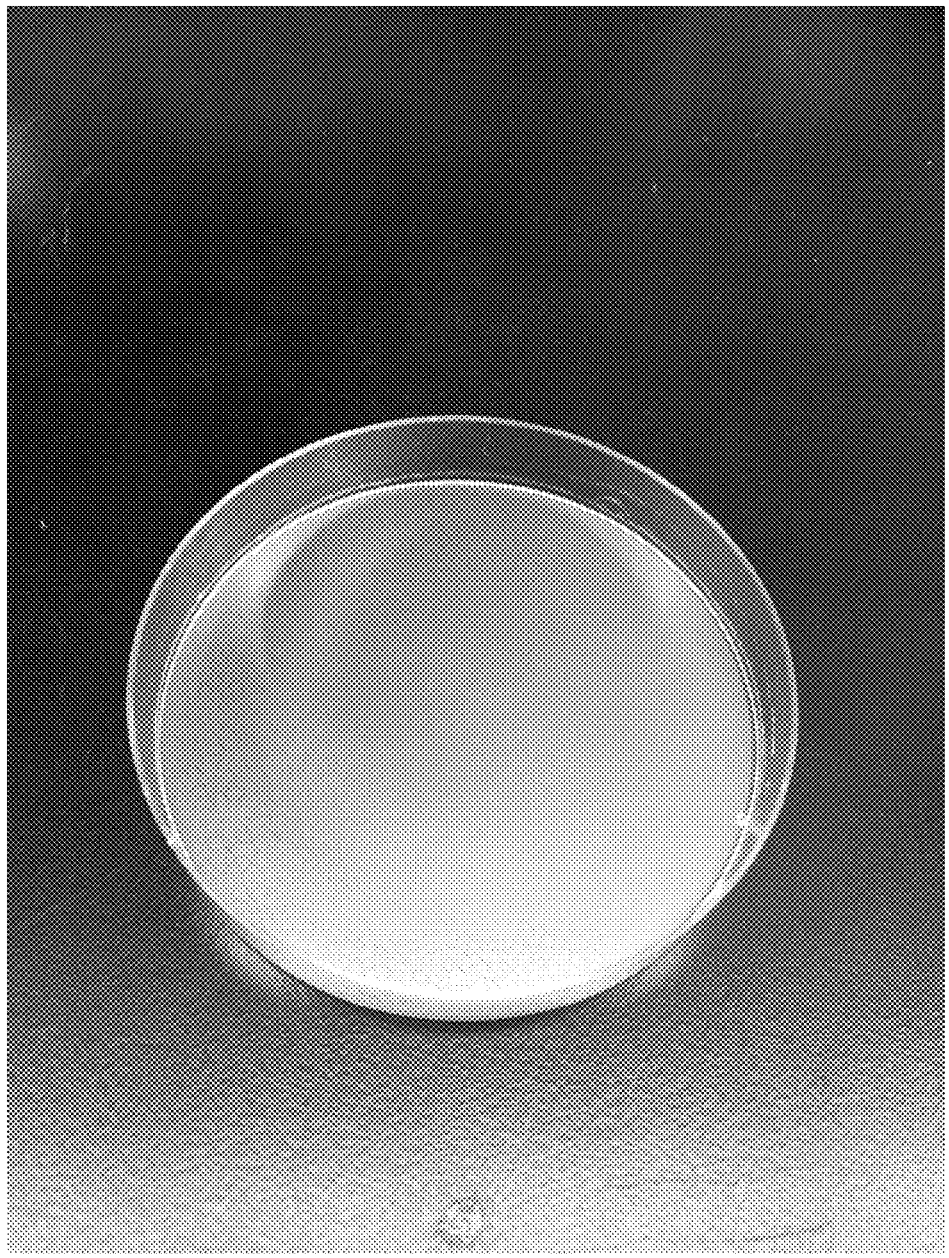
FIG. 1 is a photograph of an adherent calcium lactate film, formed by evaporation of a methanol solution containing 100 mg solubilized anhydrous calcium lactate and 4% by weight water on the interior of a 90 mm diameter Petri dish.

The present technology provides a convenient and effective method for preparing gelled growth media for culturing microorganisms. The technology makes use of the ability of pectins to gel in the presence of calcium ions, and also benefits from the discovered ability of at least one water-soluble yet non-hygroscopic calcium salt, calcium lactate, to form a fine, adherent coating on a culture vessel surface when precipitated by evaporation from a solution containing the calcium salt dissolved in a volatile organic solvent, e.g., methanol.

Pectins are rich in galacturonic acid residues, many of which are naturally ethyl-esterified. During purification from vegetable materials such as citrus peels and pulp, some of the methyl ester groups are lost, resulting in a mixture of so-called high methoxyl (HM) and low methoxyl (LM) pectins. With LM pectins the degree of methoxylation (esterification of galacturonic acid carboxyl groups) is less than 50%. Typically, about 5%-49% or more, such as about 25%-40%, of the galacturonic acid residues remain esterified, and the methoxyl content by weight of the LM pectin is between approximately 2% and 8% or less than 7% and often about 5% by weight.

A pectin-based gelling system utilizing calcium ions that can gel and solidify a nutrient medium at ambient temperature obviates the need to boil or otherwise heat or reheat a microbial culturing medium, such as one containing agar, immediately before pouring the medium into a Petri dish or similar container. The system of the present technology provides for sterile packaging of the pectin-containing medium after production. Therefore, the present technology is well suited for field work, consumer use, and lab use where controlled heating may be impossible, inconvenient, or simply take too long. The sterile package of medium can be opened at the testing site. It is known that LM pectins may be gelled using between approximately 15 mg and 30 mg of calcium ions per gram of pectin. For example, calcium chloride (containing approximately 36% by weight calcium), when used to promote pectin gelation in other systems, requires from about 42 mg to about 84 mg of $CaCl_2$) per gram pectin for gelling an aqueous medium.

While an unmodified LM pectin can be used, the use of a chemically modified LM low ester pectin that has been altered by amidating the pectin (an LA or LMA pectin) can be beneficial. The amidated pectin molecules are modified by converting some of the galacturonic acid residues to carboxylic acid amides (e.g., using ammonia) and the resulting pectins can form strong gels over a wider range of calcium concentrations than the unmodified LM pectins. The percentage of galacturonic acid residues converted to carboxylic acid amides, i.e., the "degree of amidation" for pectins useful herein generally ranges from approximately 10% to 25%. For example, LA 410 has a degree of amidation of approximately 19% and a degree of esterification of the acid groups of approximately 31% while LM 35 has a degree of amidation of approximately 15% and a degree of esterification of approximately 35%. It was found that a surprisingly wide range of calcium levels of between 10 mg and 60 mg or even as high as 90 mg calcium per gram of pectin can be used to gel the LA low ester amidated pectin gels, with surprisingly low levels of dissolved solids, without excessive syneresis occurring even 1-2 days after forming the gel.

Use of unmodified LM pectin can create issues with syneresis when only low levels of dissolved solids, a.k.a., soluble solids, are present in nutrient gels and the gels are shipped, in gelled form, causing syneresis. While unmodified LM pectin can be utilized in the present technology, advancement in the field of modified pectin is encompassed in the presently described technology. Therefore, the embodiments described herein do not limit the scope of the presently described technology to the modified pectins currently available, but the present technology anticipates that future pectins could cause firm, durable gelling with less or more calcium content. The chemically modified LA or LMA pectins are preferred.

The growth media described herein containing low methoxyl or amidated pectin is not limited in the other ingredients and may contain other ingredients such as, for example, preservatives, blood cells, pH indicators, inhibitors, neomycin, beef broth, gentamicin, indicators, soy, and buffers. The growth media described herein can be targeted for growing a specific type of organisms and might include nutrients for that organism while including inhibitors for other types of organisms.

In addition to discovering the advantage of using calcium lactate on a surface with an amidated low ester pectin to limit or fully prevent gel syneresis in Petri dishes or containers containing a pectin-gelled growth medium with a low level of dissolved solids, the present technology provides a convenient and more cost-effective method for introducing sterile calcium ions into a pectin-containing culture medium contained in a Petri dish. Another surprising result of the present technology was to find a method to produce a firm and smooth pectin gel in a short time period.

During research, for example, calcium chloride and calcium nitrate were dissolved in a number of different solvents that were applied directly to the interior surface of a Petri dish. To achieve more rapid drying and depositing of the above calcium salts in the bottom of a Petri dish, the salts were dissolved in 1 mL of denatured alcohol. Small quantities (e.g. 50 mg) of these salts were dissolved and then applied directly to the bottom interior surface of 15 mm×90 mm polystyrene Petri dishes and air dried. As the alcohol solvents evaporated, these calcium salt coatings dried as irregular spots and streaks on the bottom of the dishes, whereupon the deposited salts soon appeared visibly wet from the uptake of ambient moisture (these salts being hygroscopic or deliquescent), making the entire procedure problematic. Thereafter, when 15 mL of sterile potato dextrose broth (PDB) nutrient medium containing 2% by weight dissolved LA 410 pectin (together abbreviated "PDB-P") was poured into these 90 mm diameter Petri dishes (coated with the above-described calcium salts) the PDB-P medium immediately gelled in irregular clumps. It is believed that the deposited spots of concentrated (inorganic) calcium salts caused solubilized pectin to gel in a rapid and unpredictable manner. It was concluded that unless a calcium salt could be dried and firmly attached to a Petri dish surface and then released and dissolved slowly into the pectin-containing medium, a smooth gel could not be obtained.

After many attempts at controlling the gelling of a pectin-containing culture medium, it was surprisingly found that an edible calcium salt known as calcium lactate (Jost Chemical Company, St. Louis, Mo.) quite remarkably did not dissolve in ethanol but instead dissolved in methanol. It was also surprisingly found that a limited number of other organic salts of calcium could work with the present technology.

Surprisingly, when approximately 1.0 mL to 1.3 mL (or a range of volume from approximately 0.7 mL to 1.5 mL) of methanol solutions containing either 50 mg, 75 mg, 100 mg, or 200 mg of the dissolved anhydrous calcium lactate was applied so as to coat the bottom of 15 mm×90 mm polystyrene Petri dishes (Corning, Inc.) by tilting the dishes back and forth, the calcium lactate solutions dried as smooth and adherent uniform films. These films appeared nearly colorless and transparent in the absence of moisture or alternatively whitish and translucent (visually microcrystalline) when small amounts of moisture were present in the methanol. Advantageously, owing to the natural disinfectant property of primary alcohols including methanol (as well as ethanol and isopropanol for example), the solution of calcium lactate in methanol was self-disinfecting as were the Petri dish surfaces coated with these solutions. This disinfecting property was advantageous in obviating additional sterilization steps for the calcium lactate solution and/or the calcium lactate-coated Petri dish surfaces. Smaller and larger Petri dishes, e.g., 30 mm to 150 mm diameters, and microbe culture containers of other shapes and sizes can be conveniently coated with methanol-containing calcium lactate solutions as described above by arithmetically scaling the quantity of calcium lactate solution to be used according to the surface area to be coated.

Surprisingly, the calcium lactate, after adhering to the Petri dish after evaporation of the methanol, was not hygroscopic or deliquescent but instead was stable and durable. Therefore, an embodiment of the present technology is a Petri dish or other container with an internal coating of calcium lactate, at least upon the bottom interior surface, with the calcium lactate coating produced through evaporation of methanol or other volatile solvents such as blends of ethanol and methanol.

In a preferred embodiment, ensuring the presence of or adding about 2% to 5% by volume water to methanolic solutions of calcium lactate is desired. The presence of this small amount of water in the methanolic solution results in the calcium lactate coatings drying with a whitish translucent appearance. This is beneficial in confirming that the calcium lactate coatings are uniform across the entire surface of the Petri dish (or other cell culture container) and assures that pectin gel formation will also be uniform. By comparison, dried coatings of calcium lactate from anhydrous methanolic solutions are transparent and more difficult to monitor for coating uniformity.

The stability of the adherent calcium lactate film was surprisingly useful. When 15 mL of the same PDB-P liquid culture medium described above was either immediately or even weeks later applied over these dried films containing the above-cited 50 mg, 100 mg and 200 mg quantities of calcium lactate contained in 90 mm diameter Petri dishes (approximately 64 $cm^2$ bottom interior surface area), the films remained attached to the polystyrene (or alternatively glass) Petri dishes and slowly dissolved into the overlaid liquid medium (15 mL/64 $cm^2$ or approximately 0.25 mL per square centimeter) after several minutes time had elapsed. Within approximately 15 minutes the pectin-containing culture medium appeared to be gelled and within approximately 30 minutes the medium had firmly gelled as evident upon finger contact.

Accordingly, an embodiment of the present technology is a Petri dish or similar container containing a layer/film of calcium lactate, deposited by the evaporation of methanolic solution, at least upon the bottom interior surface, with the precoated Petri dish or container sealed and supplied in a kit with a package of pectin-containing growth media. In this embodiment, the pectin-containing growth media is pre-sterilized, the package is opened, and the growth media is poured into the Petri dish or similar container containing the layer of calcium lactate. The lid to the container is optionally applied. The calcium lactate slowly dissolves into the growth medium, causing the growth medium to gel. The present technology also encompasses a method of manufacturing a Petri dish or other container with said layer/film. The kits containing Petri dishes or containers with pre-formed calcium lactate precipitate coatings thereby obviate the need for the consumer or end user to handle and pour the methanolic solution and to form the dried coatings. Methanol is toxic, albeit this is likely a miniscule amount of methanol, and the preformed coating avoids risks of spilling the methanol solution or forming a poor calcium lactate coating that would result in poor quality pectin gel.

All four levels of calcium lactate, discussed above, enabled full gelling of 2% by weight solutions of pectins LA 410 and LM 35 dissolved in PDB culture media. After 24 hours incubation at room temperature (23° C.) the four different levels of anhydrous calcium lactate (50, 75, 100, and 200 mg) provided in 15 mm×90 mm diameter Petri dishes resulted in different amounts of syneresis as quantitated by blotting and weighing free liquid present around the circumference of the 15 mL gelled culture media in Petri dishes. For example, 15 mL of PDB-P medium gelled with 50 mg calcium lactate released essentially no free liquid (zero syneresis) after incubation at room temperature for 24 and 48 hours. By comparison, 75 mg calcium lactate-gelled PDDB medium released approximately 0.15 to 0.25 mL liquid while 100 mg calcium lactate-gelled PDB medium released approximately 0.5 to 1.0 mL liquid and 200 mg calcium lactate-gelled PDB medium released approximately 2.2 mL liquid based upon duplicate Petri dishes.

Therefore, 50 mg and 75 mg of anhydrous calcium lactate-gelled growth medium (15 mL) released little if any liquid by syneresis and are convenient usage levels for a Petri dish having an approximate diameter of 90 mm (64 $cm^2$ area or about 10 square inches). With the knowledge that anhydrous calcium lactate contains 18.4% by weight calcium, and with each Petri dish containing 0.3 g pectin (2%×15 mL) the Petri dishes contained approximately 9 mg, 18 mg and 37 mg of calcium ions respectively, representing 30 mg, 60 mg and 120 mg of calcium per gram pectin.

It is generally understood that 30 mg of calcium ions is sufficient to fully gel 1 gram of amidated low ester pectin, so it is likely that adding two and four times more calcium causes some contraction and partial collapse of the originally gelled pectin structure, thereby resulting in syneresis, i.e., the release of water. In any event, the surprising discovery that a methanolic solution of calcium lactate is able to uniformly dry and coat a Petri dish surface, where the resulting deposited and dried film remains bound to a polystyrene or glass Petri dish surface while the coating gradually dissolves into an overlaid pectin-containing culture medium could not have been predicted. Simultaneous sterilization of the container and solution was also a surprising result. The calcium lactate deposited from evaporation of methanol was surprisingly stable (for many weeks) upon the container walls. The ability to store the calcium lactate coated container for long periods of time and subsequently add the liquid growth media to the container was unanticipated.

The embodiment of a self-contained kit containing a package of pectin-containing growth media, a package of calcium lactate (or other organic salt of calcium) in methanol, and a pre-sterilized Petri dish enables another aspect of durability, transportation, and storage. If needed, the calcium lactate in methanol can be used to sterilize the container prior to evaporation of the methanol. The deposited calcium lactate is sterilized by the methanol during application.

It was subsequently found that a significant portion of the methanol solvent for anhydrous calcium lactate could be replaced by a significant portion of other miscible alcohols including but not limited to ethanol and isopropanol. These higher molecular weight alcohols are poor solvents for calcium lactate but because methanol is a very effective solvent for calcium lactate, 50% or more of the methanol may be replaced by these higher alcohols and calcium lactate will still dissolve. However, such mixed alcohol solvents evaporate more slowly than methanol alone so that a longer time interval is generally required for the calcium lactate film to dry. As a point of reference if 1.3 mL of 100% methanol containing 50-200 mg calcium lactate is applied to a 15 mm×90 mm Petri dish surface at room temperature, as little as 10-15 minutes are required to fully dry the film from the applied solution depending in part upon the ambient temperature and the relative humidity. In preferred embodiments, some water is in the calcium lactate/methanol solution, causing the subsequent calcium lactate film to have a whitish translucent appearance.

The present technology is not limited to the solvents discussed herein, but methanol surprisingly provided sterilization along with even deposition of the calcium lactate on the container walls.

The present technology is not limited to calcium lactate, and any organic calcium salt that dissolves or partially dissolves in a rapidly evaporating solvent is encompassed in the system and methods/embodiments disclosed by the present technology. The salts useful for the present technology are, in general, moderately soluble in water allowing a thin coating of the salts on a cell culture container to gradually dissolve into a cell growth medium applied over the salt coating, while preferably being highly soluble, or moderately soluble in volatile solvent(s). In some examples a slurry of calcium salt is sufficient in which case the organic calcium salt can be highly, moderately or poorly soluble in the volatile solvent. While the volatile solvent used can be other than methanol, some examples of other organic calcium salts are: calcium acetate, calcium malate, calcium citrate malate, calcium maleate, calcium lactate gluconate, calcium citrate salts combined with other salts, calcium fumarate, calcium gluconate, calcium propionate, calcium stearoyl-2-lactylate, calcium galactonate, calcium ascorbate, and combinations thereof and/or hydrates/anhydrous forms. Calcium fumarate anhydrous, calcium malate anhydrous, and calcium gluconate were tested on Petri dishes, using methanol slurries for application, and these salts smoothly gelled the pectin-containing growth medium in longer times than calcium lactate. The present technology encompasses any calcium salt that is highly or moderately soluble in a volatile solvent, for example, methanol, with or without additional calcium lactate. The present technology does not encompass non-organic salts of calcium that are highly soluble in water but not in volatile organic solvent(s). Preferably the calcium salt, such as calcium lactate, used to form the calcium salt film is moderately soluble in the gellable growth medium added to the culture container, and/or moderately soluble in water (i.e., the salt is not highly soluble in water, i.e., is preferably not calcium chloride, calcium acetate, or calcium nitrate, and preferably is not poorly soluble in water such as calcium phosphate dibasic or calcium carbonate), so as to slowly and gradually release calcium ions into the gellable growth medium consistent with the formation of a thin, uniform film of calcium salt on the growth surface of the container, which allows uniform gelation of the culture medium. A calcium salt film that is formed from a highly water soluble or heterogeneously distributed calcium salt can result in too fast a release of calcium ions into the gellable culture medium, producing a heterogeneous or poorly gelled culture medium. While these examples are not intended to limit the scope of the present technology, other combinations of volatile solvents and calcium ions are envisioned and within the scope of the present technology, which provides the system and methods necessary to include the abovementioned benefits and/or embodiments.

Another embodiment of the present technology is a system of manufacturing the sterile pectin-containing culture media and packaging the media in the correct amounts/concentrations for use in a Petri dish or similar container by an end user who has limited skills. This aspect of the technology is combined with a system of manufacturing a container of calcium lactate solution in methanol that is pre-sterilized and securely packaged in the correct concentration/amount to gel the package of pre-sterilized pectin-containing growth media. The system of manufacturing includes calculating the concentrations and amounts of pectin culture media and calcium lactate solution such that the end user does not need to consider such skills. The internal surface area of the Petri dish or container to be included in the kit is included in the calculation of the volume of calcium lactate solution packaged in the kit. The volume and concentration of calcium lactate is calculated so that gelling of the growth medium is done without the end user needing to consider these factors. This system enables quality production of a kit containing the sealed packages described above, a sterile Petri dish or similar container with instructions. The kit can be sealed and stored, shipped, or immediately used. Various kits can be provided depending on the intended organism to be grown upon the growth media in the kit.

In yet another embodiment of the present technology, sterilization of the entire kit and contents is performed after assembly of the kit by, for example, irradiation or microwaves. In this example the kit and contents are sterilized before shipment to the end user.

Another aspect of the present technology is a method of using the kit. For example, the end user, who may be a person of ordinary skill, opens the kit, opens the Petri dish, and opens the container of calcium lactate solution. The end user places the Petri dish on a level surface and pours the calcium lactate solution into the Petri dish, next ensuring the Petri dish has an evenly distributed coating of the solution at least entirely upon the bottom interior surface. The end user waits a brief time for the methanol to evaporate, thereby forming an even coating of calcium lactate at least upon the bottom interior surface of the Petri dish (see FIG. 1). The end user then opens the package of sterile, pectin-containing culture medium and pours the medium into the Petri dish. The lid to the Petri dish is then immediately applied. After waiting a brief period of time, e.g., 15-30 minutes, the pectin-containing culture medium forms a gel. The end user then follows instructions for sampling and/or placing a test specimen onto the sterile growth medium.

If, for example, the end user is provided a sterile culture container with an pre-applied internal coating of calcium lactate, the end user could be instructed to add the pectin-containing growth media and await gelling.

The methods described above are not limited by the examples provided. For example, the calcium lactate solution can be provided in a breakable package within a container with a flexible pressure point, and the end user merely applies pressure to the breakable package, releasing the calcium lactate solution. After methanol evaporation, the growth media can be applied to the calcium lactate film.

Figure 2:
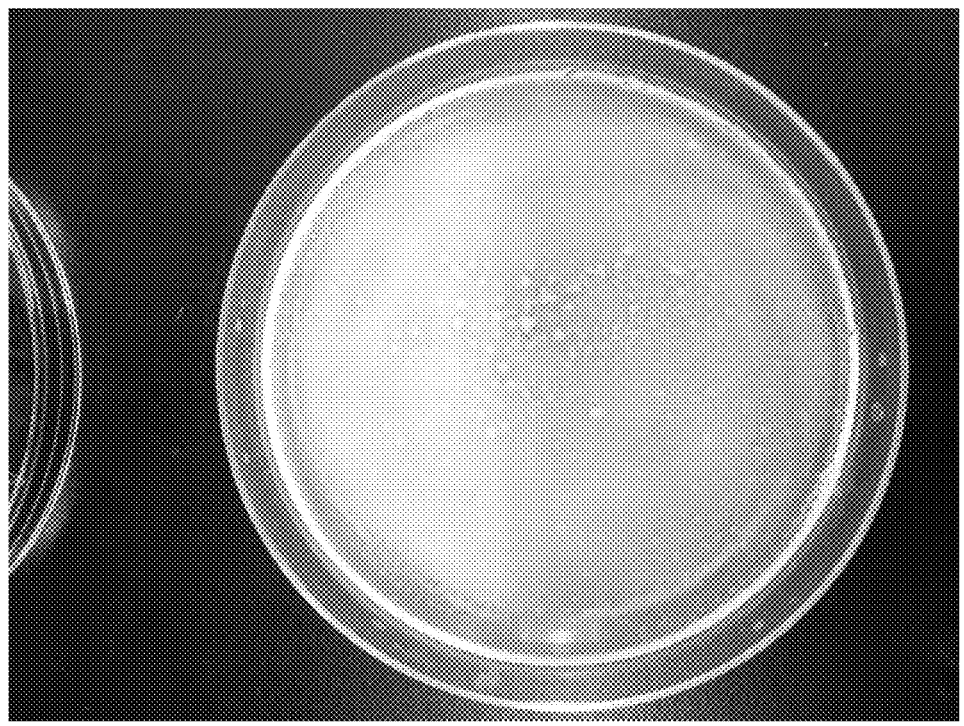
FIG. 2 is a photo of an adherent coating of 100 mg anhydrous calcium malate powder, deposited by evaporation of a methanol slurry of the salt particles on the interior of a 90 mm diameter Petri dish.
Figure 3:
FIG. 3 is a photo of an adherent coating of 200 mg anhydrous calcium gluconate powder, deposited by evaporation of a methanol slurry of the salt particles on the interior of a 90 mm diameter Petri dish.

Instead of calcium lactate, a slurry/suspension of a different organic salt of calcium can be used, for example, a slurry of a fine powder of calcium fumarate anhydrous, calcium malate anhydrous, or calcium gluconate. When a slurry is used, the end user tilts a Petri dish (or other container) containing the slurry back and forth to uniformly coat the bottom of the dish and then allows the slurry to dry. After drying, approximately 15 mL of a culture medium is poured into a 90 mm diameter Petri dish and a pectin-containing cell growth medium may gel over a longer period of time compared to the gel-time for calcium lactate. The calcium salt coatings formed in Petri dishes or other containers from methanolic suspensions/slurries are not as uniform as the coatings formed from calcium lactate but are adequate for the purpose of evenly gelling a culture medium (e.g., see FIGS. 2 and 3 compared to FIG. 1).

Petri Dish or Container Selection

The Petri dish or container can be disposable or reusable and some examples of suitable materials include polystyrene resin, polylactide resin, or glass. The Petri dish or container can be made of various rigid materials such that a shallow cylindrical or other shaped dish is provided with an optional lid. The Petri dish or container should be relatively inert with respect to the alcohol and solutes added so that structural integrity is maintained. The shape of the container can be changed to suit the growth conditions or sampling conditions. The container is typically transparent, but opaque or translucent materials are encompassed because, for example, a light sensitive organism could be growing on the culture medium. The lid could be configured for specific environmental sampling or configured to enable organism growth upward. The present technology is not limited by the composition of the Petri dish or container, and the examples provided herein are for illustrative purposes only. Pre-sterilized Petri dishes can be purchased for use in manufacturing/providing the kits described herein.

In some examples, the Petri dish or container may be made of glass or borosilicate, ethylene vinyl acetate (EVA) polymers, ethylene methyl acrylate (EMA) polymers, polyethylenes [including, for example, low density polyethylene (LDPE), linear low density polyethylene (LLDPE), high density polyethylene (HDPE), and ultra-high molecular weight polyethylene (UHMWPE), polypropylenes, ethylene-propylene rubbers, ethylene-propylene-diene rubbers, polystyrene, poly (1-butene), poly(2-butene), poly(l-pentene), poly(2-pen-tene), poly(3-methyl-1-pentene), poly(4-methyl-1-pentene), 1,2-poly-1,3-butadiene, 1,4-poly-1,3-butadiene, polyiso-prene, polychloroprene, poly(vinyl acetate), poly(vinylidene chloride), poly(vinylidene fluoride), poly(tetrafluoroethyl-ene), and the like, and combinations thereof. The lid of the Petri dish or container can optionally be made of similar material or designed for specific sampling/growth purposes.

In other examples, the Petri dish or container may be made of polymers including olefin homopolymers and copolymers (especially, polyethylenes, polypropylenes, ethylene vinyl acetate polymers, and combinations thereof). Other polymers include olefin homopolymers and combinations thereof (polyethylenes and combinations thereof; ultra-high molecular weight polyethylenes (UHMWPE) and combinations thereof). The lid of the container or Petri dish can be made of a material different from the lid or of various materials.

In alternative examples, the Petri dish or container is not rigid and is flexible so that the calcium lactate solution and/or growth media can be contained inside of the flexible container. In these examples, the calcium lactate solution and/or growth media is released from a breakable package within the flexible container package.

In some embodiments, the Petri dish or container is specially designed in shape/configuration to trap organisms and/or to prevent entry of certain organisms.

FIG. 1 shows a photo of a 90 mm diameter polystyrene Petri dish with an interior film coating of calcium lactate formed and deposited by evaporation of a solution containing 1 mL methanol, 100 mg calcium lactate anhydrous and 4% by weight water, in which the resulting coating is suitable for gelling a pectin-containing growth medium. The Petri dish was tilted back and forth to uniformly coat the bottom of the dish and then allowed to dry on a flat surface.

FIG. 2 shows a photo of a 90 mm diameter polystyrene Petri dish with an interior coating of calcium malate powder deposited by evaporation of a slurry containing 1 mL methanol and 100 mg calcium malate anhydrous particles, in which the resulting coating is suitable for gelling a pectin-containing growth medium. The Petri dish was tilted back and forth to uniformly coat the bottom of the dish and then allowed to dry on a flat surface.

FIG. 3 shows a photo of a 90 mm diameter polystyrene Petri dish with an interior coating of calcium gluconate powder deposited by evaporation of a slurry containing 1 mL methanol and 200 mg calcium gluconate anhydrous particles, in which the resulting coating is suitable for gelling a pectin-containing growth medium. The Petri dish was tilted back and forth to uniformly coat the bottom of the dish and then allowed to dry on a flat surface.

Definitions

As used herein "methanolic" solutions are any solutions containing at least some methanol ranging up to solutions containing mostly or entirely methanol, such as solutions that contain 5-100 volume % of methanol and the remainder of water or another miscible solvent that can be removed by evaporation or other convenient mechanism. Likewise, the methanol slurries disclosed herein are slurries that may contain at least some methanol ranging up to slurries containing mostly or entirely methanol. A "solution comprising calcium lactate and methanol" may also contain any amount of water or other ingredients. Slurries of organic salts of calcium in methanol may also contain any amount of water or other ingredients.

As used herein "growth media" and "growth medium" can be any mixture that sustains or nourishes growth of one or more organisms such as bacteria, molds or viruses and the mixture may be designed to prevent growth of other organisms.

As used herein "excessive syneresis" (release of free liquid from the gel) refers to release of free liquid to such an extent that it may interfere with some experiments involving microorganisms, generally undesirable for measurements, yet it could potentially be considered non-interfering for other biological growth conditions, for example, for some eukaryotic cells. While excessive syneresis is not desirable for traditional bacterial/fungal colony growth in Petri dishes, excessive syneresis might be desirable for growth of some other biological organisms, so the definition is not construed so as to limit the present technology in the scope of different gels formed or different ingredients used.

As used herein "Petri dish" or "container" describes a container that will contain a coating of a suitable calcium salt such as calcium lactate after evaporation of a calcium lactate solution in methanol or similar volatile solvent. The Petri dish or container can be flexible or rigid, opaque, transparent, or translucent. The Petri dish or container may have a lid or be entirely self-contained, without lid. The surface area of the container should be calculable at one static condition because the amounts and concentrations of the calcium lactate solution(s) described herein must be calculated for appropriate usage with the container and simultaneously calculated for appropriate gelling of the culture growth media, but the container can be expandable with changing surface area(s). Thus, the container can be inflatable or compressible and can change shape if needed.

As used herein "volatile solvent" includes any organic solvent that, when 1 mL is placed into the bottom of an open dry Petri dish with approximately 90 mm diameter, will evaporate to dryness in less than 1 hour or even a substantially shorter time such as 10-20 minutes at a temperature of 25° C. and a relative humidity of 10%.

As used herein "highly soluble" refers to a solute that is soluble in a solvent at greater than or equal to 10% by weight. "Moderately soluble" refers to a solute that is soluble in a solvent at from 1% to less than 10% by weight. "Poorly soluble" refers to a solute that is soluble in a solvent at less than 1% by weight. All solubilities are as determined at 25° C.

As used herein a "slurry" is a suspension of a fine powder in a solvent, wherein the powder may be either highly, moderately or poorly soluble in the solvent.

As used herein any other organic salt of calcium can be substituted in place of the term "calcium lactate" as other organic salts of calcium are within the scope of the present technology and several have been tested with success (FIGS. 2 and 3).

Those with skill in the art would readily appreciate that the present technology is well adapted to obtain the ends and advantages mentioned, as well as those inherent therein. The systems, methods, usages, kits, variances, and compositions described herein as presently representative of preferred embodiments are exemplary and are not intended as limitations on the scope of the technology. Changes therein and other uses will occur to those skilled in the art, which are encompassed within the ideas of the technology, are defined by the scope of the claims. Changes envisioned but not fully discussed are providing the present technology with a means of heating or cooling for example hot packs or cold packs so that the present technology may be used in cold or hot environments, providing the present technology with an attractant that attracts specific organisms, or alternatively a repellant. Some other examples not fully discussed are modifications to the kit enabling usage in extreme environments.

The technology illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the technology claimed. Thus, it should be understood that although the present technology has been specifically disclosed by preferred embodiments and optional features, modification and variation of the concepts herein disclosed may be resorted to by those skilled in the art, and that such modifications and variations are considered to be within the scope of this technology as defined by the appended claims.

In addition, where features or aspects of the technology are described in terms of kits, groups or other grouping of alternatives, for example packages, methods, containers, lids, order of sterilization, those skilled in the art will recognize that the technology is also thereby described in terms of any individual member or subgroup of members of the methods, kit, group, containers, lids, orders of sterilization or other alternative grouping of the kits, methods, and physical embodiments.

Also, unless indicated to the contrary, where various numerical values or value range endpoints are provided for embodiments, additional embodiments are described by taking any 2 different values as the endpoints of a range or by taking two different range endpoints from specified ranges as the endpoints of an additional range. Such ranges are also within the scope of the described technology. Further, specification of a numerical range including values greater than one includes specific description of each integer value within that range.

Thus, additional embodiments are within the scope of the technology and within the following claims while the concepts of the systems, methods, and kits described herein are broadly applicable to moving the provision of biological culture media into farther reaches.

What is claimed is:

1. A method for preparing a gelled biological growth medium, the method comprising:
   a) providing a container for culturing microorganisms and a solution comprising calcium lactate and methanol;
   b) depositing the solution onto a growth surface of the container;
   c) allowing the solution to evaporate, thereby forming a calcium lactate precipitate on the growth surface;
   d) coating the calcium lactate precipitate with a liquid growth medium comprising low methoxyl pectin; and
   e) allowing the liquid growth medium to gel, thereby forming the gelled biological growth medium.

2. The method of claim 1, wherein the low methoxyl pectin is a low methoxyl amidated pectin and is the sole gelling agent.

3. The method of claim 1, wherein the low methoxyl pectin has a methoxyl content of from about 2% to about 8% by weight.

4. The method of claim 3, wherein the low methoxyl pectin has a methoxyl content from about 5% to about 6%.

5. The method of claim 1, wherein the liquid growth medium comprises from about 10 to about 30 grams of pectin per liter.

6. The method of claim 1, wherein the container is a thermoplastic or glass Petri dish.

7. The method of claim 6, wherein the Petri dish comprises polystyrene or polylactide.

8. The method of claim 1, wherein the solution comprising calcium lactate and methanol comprises calcium from about 10 to about 60 milligrams of calcium per gram of low methoxyl pectin present in the liquid growth medium.

9. The method of claim 1, wherein the calcium lactate precipitate comprises calcium from about 10 to about 60 milligrams of calcium per gram of low methoxyl pectin present in the liquid growth medium.

10. The method of claim 1, wherein the solution comprising calcium lactate and methanol further comprises between about 2% and 5% water by volume.

11. The method of claim 1, wherein the liquid growth medium is selected from the group consisting of potato dextrose broth, yeast extract dextrose broth, and combinations thereof.

12. The method of claim 1, wherein the liquid growth medium further comprises an antimicrobial agent that selectively inhibits growth of one group of microbes while permitting growth of another group of microbes.

13. The method of claim 12, wherein the liquid growth medium comprises from about 50 to 100 micrograms per milliliter of chloramphenicol to inhibit growth of bacteria while permitting growth of yeast and mold.

14. The method of claim 1, wherein the container is sterilized by the methanol.

15. The method of claim 1, wherein the container is a Petri dish, and wherein the solution comprising calcium lactate and methanol is added to in an amount from about 0.5 mL to 2 mL per 64 $cm^2$ area of the growth surface.

16. The method of claim 1, wherein the solution comprising calcium lactate and methanol comprises from about 25 to about 100 volume % methanol.

17. The method of claim 1, wherein the solution comprising calcium lactate and methanol comprises from about 85 mg to about 350 mg of anhydrous calcium lactate per gram of the low methoxyl pectin.

* * * * *